United States Patent [19]

Enhorning

[11] Patent Number: 5,224,494
[45] Date of Patent: Jul. 6, 1993

[54] VAGINAL PESSARY

[76] Inventor: Goran E. Enhorning, 21 Oakland Pl., Buffalo, N.Y. 14222

[21] Appl. No.: 854,331

[22] Filed: Mar. 19, 1992

[51] Int. Cl.⁵ .............................................. A61F 6/06
[52] U.S. Cl. .................................. 128/834; 128/836; 128/837
[58] Field of Search ....... 128/885, 834, 830, DIG. 25, 128/836, 837; 600/29-31; 606/191, 192, 193, 194, 195

[56] References Cited

U.S. PATENT DOCUMENTS

| | | |
|---|---|---|
| 1,926,518 | 9/1933 | Findley .............................. 128/834 |
| 2,494,393 | 1/1950 | Lamson . |
| 2,638,093 | 12/1959 | Kulick . |
| 3,066,667 | 10/1960 | Berry . |
| 3,080,865 | 3/1963 | Vincent . |
| 3,503,400 | 3/1970 | Osthagen ................... 128/DIG. 25 |
| 3,554,184 | 1/1971 | Habib . |
| 3,646,929 | 3/1972 | Bonnar . |
| 3,705,575 | 12/1972 | Edwards . |
| 3,866,611 | 2/1975 | Baumrucker . |
| 4,019,498 | 4/1977 | Hautrey et al. . |
| 4,019,499 | 4/1977 | Fitzgerald ............................ 600/30 |
| 4,139,006 | 2/1979 | Corey ................................... 600/29 |
| 4,290,420 | 9/1981 | Manetta . |
| 4,428,365 | 1/1984 | Hakky . |
| 4,785,828 | 11/1988 | Maurer . |
| 4,823,814 | 4/1989 | Drogendijk ....................... 128/834 |
| 4,848,363 | 7/1989 | Cattanach ......................... 128/834 |
| 4,875,898 | 10/1989 | Eakin ........................... 128/DIG. 25 |
| 4,920,986 | 5/1990 | Biswas . |
| 5,007,894 | 4/1991 | Enhorning . |

FOREIGN PATENT DOCUMENTS

| | | |
|---|---|---|
| 0152343 | 7/1953 | Australia ............................ 128/836 |
| A274762 | 7/1988 | European Pat. Off. . |
| 0463330 | 7/1928 | Fed. Rep. of Germany ...... 128/836 |
| 0569645 | 2/1933 | Fed. Rep. of Germany ...... 128/836 |
| 0078198 | 11/1949 | Switzerland ........................ 128/836 |
| 1115727 | 5/1968 | United Kingdom . |

OTHER PUBLICATIONS

Milex "19 Common Uses of the Milex Supportive Pessary" (Aug., 1990).

Primary Examiner—Michael A. Brown
Attorney, Agent, or Firm—John C. Thompson

[57] ABSTRACT

A vaginal pessary (10 or 34) used to control urinary incontinence or a prolapse, which pessary has a hollow annular body (12 or 36) and an elongated fluid conveying flexible elongated tube (16) which may be stored between the upper and lower surfaces of the annular body when the pessary has been properly inserted into the vagina. The annular body is provided with a diaphragm (20) attached to the inner surface (12.2 or 36.2) of the body, the diaphragm having a central aperture (22). The tube (16) has a coiled shape by making the tube from an elastic material having a memory, by having the tube carry a spring wire (18) forming into a coiled shape, or both. In the illustrated embodiments, a one way valve (24) is provided in an end portion (16.2) of the tube. The valve may be opened by inserting a hypodermic needle carried by a syringe to either cause the body (16) to assume its normal operational volume or to have its volume reduced for insertion or removal. After the annular body has been inserted and it is has attained its normal operational volume, the tube is released and it returns to its coiled shape, retracting into the vagina. Digital manipulation may encourage the coiled tube to fully retract. When the pessary is to be removed, a finger, directed through loops of the coil, will pull out the tube with its valve which reaches well outside the vagina for easy attachment to a hypodermic needle. Fluid may now be withdrawn from the annular body, thereby permitting easy removal.

9 Claims, 2 Drawing Sheets

VAGINAL PESSARY

FIELD OF THE INVENTION

The present invention relates generally to a vaginal pessary which is used to control urinary incontinence or a prolapse, and more particularly to an inflatable and deflatable vaginal pessary having an inflatable annular body and an elongated inflation tube, the pessary being so designed that the inflation tube may be stored between the upper and lower surfaces of the annular body when the pessary has been properly inserted into the vagina and inflated.

BACKGROUND OF THE INVENTION

Relaxation of the pelvic tissue may result in prolapse of either the uterus, bladder, rectum, or intestines; it may result in stress incontinence; or it may result in a combination of the above. Surgery will effectively control the condition; but if the patient is very old, or for other reasons is a poor operative risk, a vaginal pessary may be considered. However, in this group of women, the introitus, the inlet to the vagina, may be narrow making it painful to insert the pessary. A pessary used as a prolapse device must be as large as possible to serve as a mechanical barrier, preventing the organs from being extruded through the introitus.

Various prolapse devices have been in use for several decades. They are usually made of a solid material and, to ensure that they function adequately, they have to be as large as possible. That makes it difficult and painful to insert the device and then remove it for cleaning. These devices will, if they are made inflatable, be possible to deflate to a small size for easy insertion and then inflate so that they return to normal shape and rigidity once they are in the right location. For this reason an inflatable prolapse device, the "Inflatoball", has been on sale from Milex Products, Inc., 5915 Northwest Highway, Chicago, Ill. 60631. The mechanism for deflation and inflation of the "Inflatoball" includes a tube attached to a spherical body, which tube extends to just outside the vagina when the spherical body has been properly inserted. The tube ends with a valve which can be readily opened for deflation. It can also be connected with a pump when inflation is desired. In order to minimize the discomfort caused by the tube protruding from the vagina, the tube connected to the spherical body is very short, which for many patients makes it difficult to connect the pump.

A vaginal pessary used for control of urinary incontinence also needs to be large to perform well. As a consequence, insertion and removal of the incontinence device can also be painful. An inflatable pessary for controlling incontinence, particularly stress incontinence, is disclosed in U.S. Pat. No. 5,007,894 issued on Apr. 16, 1991. The device consists of an inflatable oval-shaped body with two projections, the oval-shaped body being provided with a central aperture to allow drainage to migrate from the uterus and out of the vagina. The two projections offer support on each side of the urethra and prevent the device from exerting a direct pressure on the urethra. This pessary, with the exception of the two projections used for control of urinary incontinence, is somewhat similar to prior art devices, in the form of donuts, used for control of vaginal prolapse.

Other prior art prolapse devices which have been used to control incontinence, and which have inflatable portions, are shown in U.S. Pat. Nos. 3,646,929, 2,638,093, and 4,920,986, British patent 1,115,727 and European Patent Application 0 274 762. All of these devices have a tube which extends out of the vagina, which tubes will cause discomfort to the wearer.

As mentioned above, an inflatable pessary is for sale but has not been widely accepted. Clearly, the urinary incontinence ring, as well as the pessary used to control a prolapse, need to have a system for inflation and deflation that will not cause the patient discomfort; in fact, it should not be noticeable to the patient once the device has been inserted into the vagina. No tubing should protrude from the vagina. The device described with this application fulfills these needs.

OBJECTS AND SUMMARY OF THE INVENTION

It is an object of the present invention to provide a vaginal pessary which may be easier to insert and to remove for cleaning, which pessary is intended for control of urinary incontinence and prolapse of the uterus, bladder, rectum, and intestines, and which vaginal pessary does not give the wearer the discomfort of prior art vaginal pessaries.

More specifically, it is an object of the present invention to provide a vaginal pessary which is inflatable, making it possible to insert it when deflated and not inflate it to normal size until it had been inserted, which vaginal pessary does not have any tubes protruding from the vagina when the pessary has been properly inserted, thereby causing less discomfort.

It is a further object of the present invention to make it possible to quickly change the size of a vaginal pessary or the like by making it small when it is to be inserted, by making it large once it is in place, and then by making it small again before it is removed, which objects are accomplished in a manner which will not cause excessive discomfort or embarrassment to the wearer of the pessary.

In summary, this change in size is accomplished by deflating and inflating an annular (or donut) shaped pessary. In accordance with this invention, a diaphragm with a large central perforation or aperture is attached to the inner circumference of the pessary. A coiled tube, which when extended is 10 inches (25 centimeters) long, is permanently attached to the inflatable pessary. At the end of the tube is a valve which is normally closed but will open up when the needle of a syringe is inserted. By applying suction with the syringe the pessary is deflated before it is inserted into the vagina. Once in place it is expanded to normal size. The syringe is then disconnected which causes the valve to close. When the tube is released it returns to the coiled shape, as the tube is made from a material having a coiled to the coiled shape and retracts into the vagina. The tube is made, at least in part, from a material having a memory of a coil, hereinafter referred to as a coil memory. Digital manipulation may encourage the coiled memory, and the tube tends to retract into the vagina. Digital manipulation may encourage the coiled tube to fully retract to the center of the pessary, the tube resting on the shelf-like diaphragm after passing through the aperture in the diaphragm. The inflation tube will not be noticeable to the patient once the inserted pessary has been expanded to normal size and the tube is resting on the shelf formed by the diaphragm. Once inserted the pessary used for control of prolapse or stress incontinence should cause no discomfort and it should immediately relieve the patient of her problem. When the pessary is to be deflated for removal; a finger, directed through loops of the coil, will pull out the tube with its valve which reaches well outside the vagina for easy attachment to a syringe. The pessary can be removed for cleaning every evening but it can also remain inserted for longer periods of time. (Pessaries are often left in the vagina for a month at a time).

The foregoing will become more apparent after a consideration of the following detailed description taken in conjunction with the accompanying drawings in which two separate forms of this invention are illustrated.

DETAILED DESCRIPTION OF THE FIRST EMBODIMENT

In the following description, reference to the parts of the prolapse pessary will be generally to their position when the device has been inserted into a patient's vagina.

Figure 1:
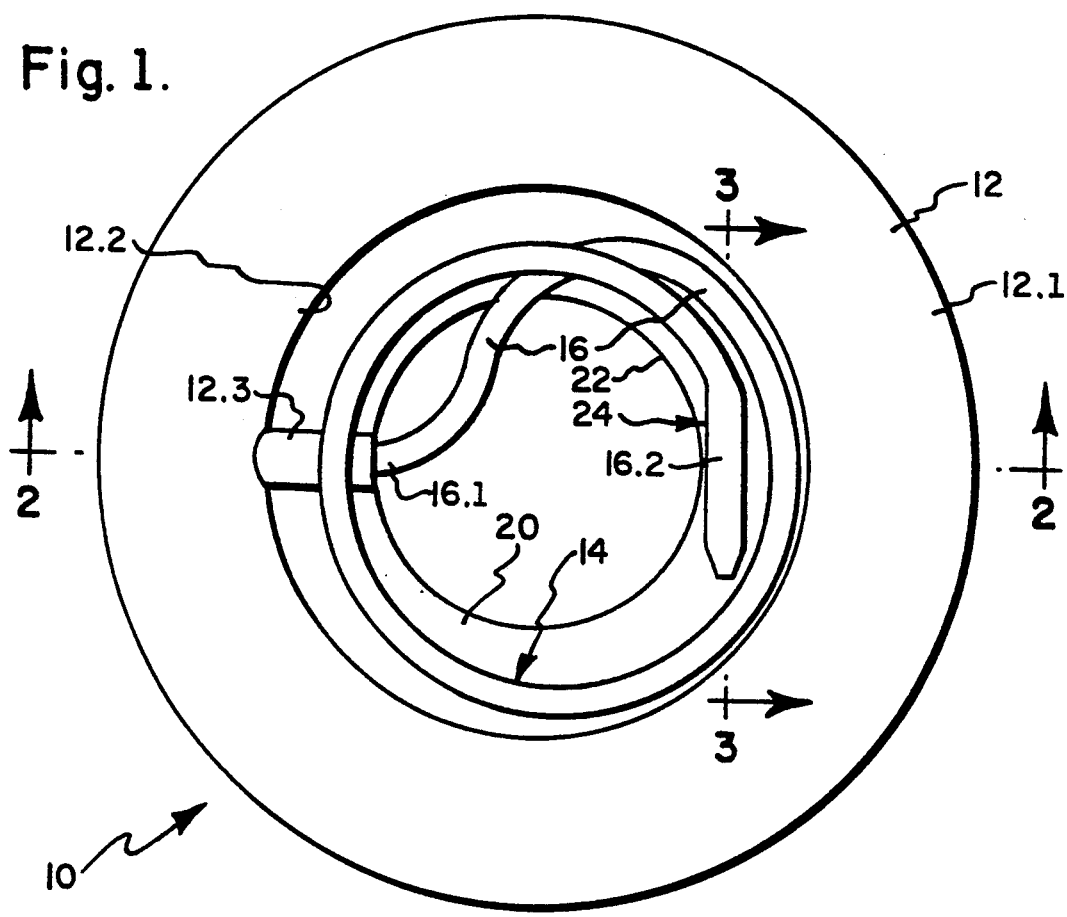
FIG. 1 illustrates a prolapse vaginal pessary in which the principles of the present invention have been incorporated, the pessary including an inflatable donut shaped body and an elongated inflation tube.
Figure 2:
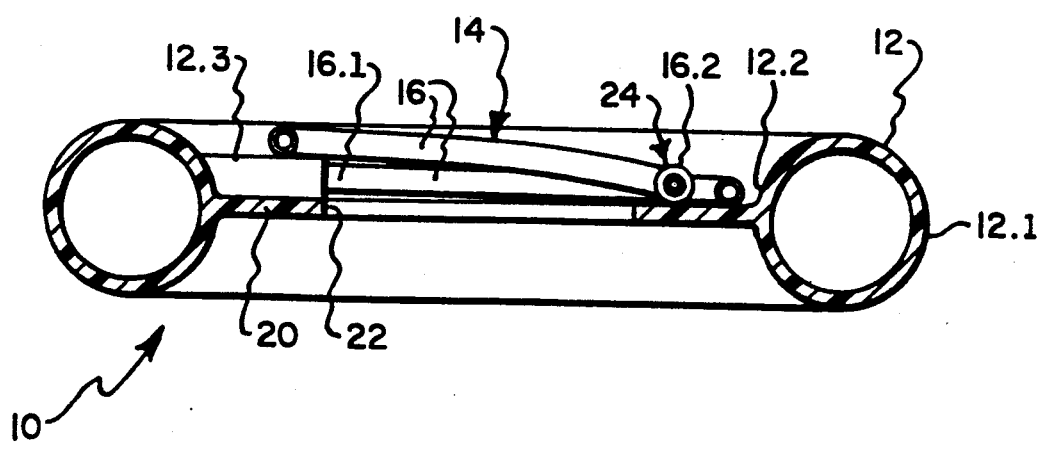
FIG. 2 is a section taken generally along the lines 2—2 in FIG. 1.
Figure 3:
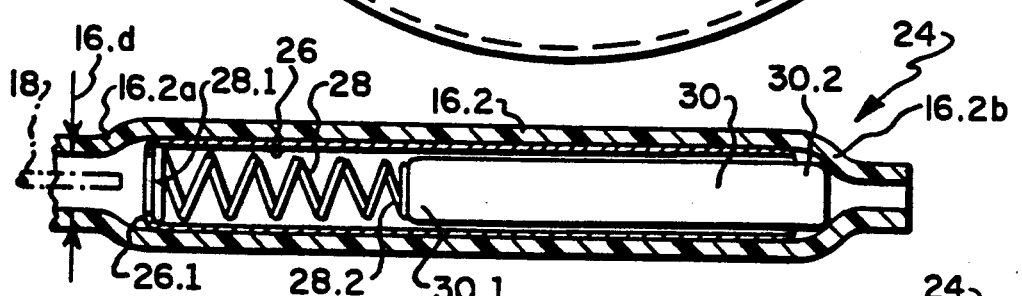
FIG. 3 is an enlarged sectional view taken generally along the line 3—3 in FIG. 1 showing the construction of the valve at the end of the elongated inflation tube, the valve being shown in a closed position.

The principles of the present invention are illustrated in the first embodiment when applied to prolapse pessary shown in FIGS. 1 and 2. The prolapse pessary, which is indicated generally at 10, is shown in a standard donut configuration. Thus, the prolapse pessary has inflatable annular body 12 which has an external surface area 12.1 and internal surface area 12.2. Elongated means, indicated generally at 14, are provided for inflating and deflating the inflatable annular body. The elongated means, which include fluid passageway means in the form of an elastic elongated tube 16, has a length sufficiently long so that when the body 12 of the prolapse pessary is properly inserted into the vagina, the elongated means will extend outwardly of the vagina a sufficient distance so that it can be easily connected to a means for inflating or deflating the body. Thus, the length of the tubing should preferably be of such a length that the free end of the elongated means extends outwardly the vagina a distance from 5 to 15 centimeters. This will ensure that the inflating means can be easily connected to the elongated means. If the tube projected out of the vagina when the pessary was properly installed, it can be appreciated that this would cause some discomfort and embarrassment to the wearer. Therefore, in order to overcome the disadvantages of this design, means are provided for maintaining the elongated means within the vagina once the inflatable vaginal pessary has been properly inserted. The means for maintaining the elongated means within the vagina may include having the elongated tube 16 assume a coiled shaped when released, an apertured diaphragm means within the vagina includes preferably both a coil means and apertured diaphragm. The elongated tube 16 will assume a coiled shape when released due to the coil memory of the tube. The coiled shape of the, or, preferably, both. The coiled shape of the elongated tube may be accomplished by making the tube of a resilient material provided with a memory. For example, the elongated tube may be made from a medical grade polyurethane, which polyurethane tubing is made with the coil memory shown in FIG. 1. Alternatively the polyurethane tube may carry a spring wire which will impart the desired coil shape to the elongated tube, the wire being shown in phantom in FIG. 3 at 18, this construction also having a coil memory. The diaphragm, which is indicated at 20, extends between interior surfaces 12.2 of the annular body 12, the diaphragm being provided with aperture 22.

The elongated tube has a first end 16.1 which is connected to the inflatable annular body 12. To this end, the body 12 is provided with a short stem 12.3 and the first end of the tube 16.1 is heat sealed within the stem to form an airtight connection. The elongated tube also has a second free end 16.2. The overall length of the tube when fully extended may be in the neighborhood of 10 inches or 25 centimeters. Thus, the elongated tube is of such a length that when fully extended it will extend out of the vagina a distance sufficiently great that it can be easily connected to a device for inflating or deflating it.

Figure 5:
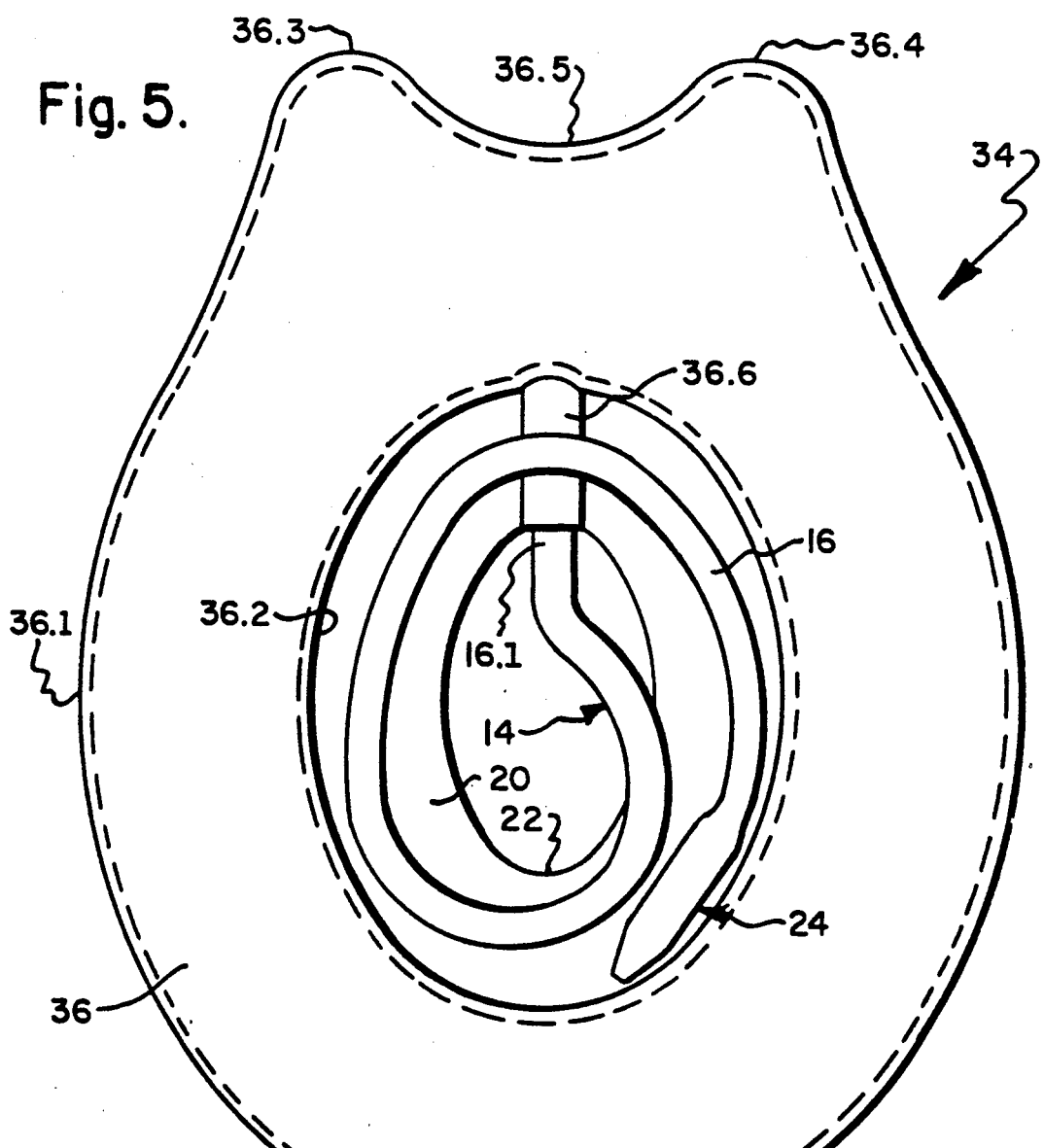
FIG. 5 is a view somewhat similar to FIG. 1 but showing the principles of the present invention incorporated into a stress incontinence pessary of the type shown in U.S. Pat. No. 5,007,894.
Figure 4:
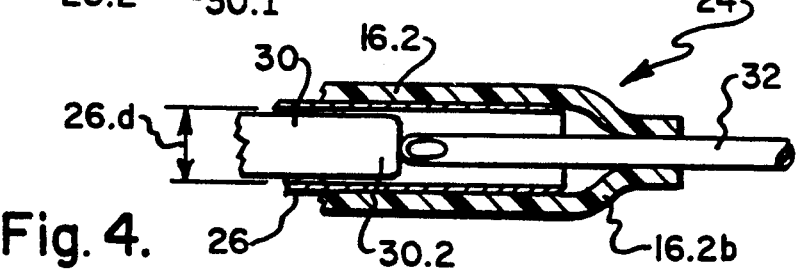
FIG. 4 is a partial sectional view somewhat similar to FIG. 3, but showing how the valve may be opened for either introducing air into the inflatable donut shaped body or for withdrawing air from the inflatable body.

The elongated means 14 includes not only the elongated tube, but also valve means in the form of a normally closed valve assembly indicated generally at 24, the valve assembly being disposed within the free end 16.2 of the elongated tube. The valve assembly includes a rigid tube 26, which may be made of stainless steel. As can be seen the rigid tube 26 is entirely disposed within the free end portion 16.2 of the elongated tube. The rigid tube has an internal diameter 26d greater than a portion of the internal diameter 16d of the elastic elongated tube. Therefore, each of the first and second portions 16.2a and 16.2b of the elastic tube which are disposed to the sides of the rigid tube 26 will have a tapered inner surface which extends from the diameter 16d to a diameter equal to the diameter of the rigid tube 26. The tube 26 is also provided with a flanged end 26.1, the flanged end having a rounded corner to facilitate entry of the rigid tube 26 within the elastic tube 16. A spring 28 is positioned within the rigid tube, the spring having a first end 28.1 which bears against the flanged end 26.1 of the tube 26, the spring also having a second end 28.2. A valve 30, which may be in the form of a stainless steel rod, is positioned within the rigid tube 26, the rod being of a diameter where it is free to slide within the tube. The second end 28.2 of the spring will bear against the end 30.1 of the valve to force the second end 30.2 of the valve into a closing relationship with the tapered surface of portion 16.2b of the tube. The end 30.2 also has a rounded corner so that it will not damage the portion 16.2a of the elastic tube when it engages to portion 16.2a to form a seal. Thus, a very simple valve has been developed which will be normally closed. However, the valve can be opened very easily. To this end it is proposed to open the valve by introducing a hypodermic needle 32 (FIG. 4) into the free end of the elongated means to force the valve or rod 30 against the spring 28, and to then introduce or remove air from the inflatable body 12. The hypodermic needle may be a blunt 16G size which is carried by a standard syringe. With reference now to FIG. 5, a stress incontinence pessary is illustrated in this figure, the stress incontinence pessary being indicated generally at 34. In this design the inflatable annular body 36 has an oval shape, rather than a donut shape. While the stress incontinence pessary of FIG. 5 has a function somewhat different than the prolapse pessary of FIG. 1, in all other respects, other than its specific shape, it embodies the same invention. Thus, it is provided with essentially the same elongated means 14 for inflating and deflating the body section 36, which elongated means is provided with both the elongated tube 16 and the normally closed valve assembly 24. In addition, it is also provided with a diaphragm 20 which extends between the interior surfaces 36.2 of the body 36, the diaphragm having an aperture 22, which diaphragm will support the elongated means 14 in a shelf like manner when the stress incontinence pessary is fully inserted. The manner of insertion and removal of the body 36 and the elongated means 14 are essentially the same as the first embodiment described above. However, as the exterior surface 36.1 of the body is further provided with two projections 36.3 and 36.4, there being a generally U-shaped surface 36.5 between the two projections, it is essential that the body be positioned with the projections lying to either side of the urethra. This pessary will function in the same manner as the incontinence device disclosed in U.S. Pat. No. 5,007,894, the subject matter of which is incorporated herein by reference thereto. In this regard, it should be noted that, normally, the lumen of the upper urethra has a pressure which, due to muscle tone, is clearly exceeding intravesical pressure. When intra-abdominal pressure is suddenly and substantially raised, as during coughing, it must be transmitted not only to the bladder but also to the upper urethra. Thereby pressure will remain higher in the urethra than in the bladder even at the peak of a cough. When stress incontinence has developed there is no longer a complete transmittance of pressure from the abdomen to the urethra, and as a result closure pressure, the difference between the highest intra-urethral and the simultaneous bladder pressure, is reduced during coughing. It may diminish all the way to zero, which causes leakage to be observable. To test the likelihood that an operation will be successful many perform the Bonney maneuver. Support is then given on each side of the urethra so that the tissue between the points of support will act as a hammock and offer counter pressure during coughing. Bonney's maneuver, with which support on each side of the urethra is offered digitally or with an instrument, will usually alleviate or totally eliminate the leakage which previously was observed to occur with coughing. The device shown in FIG. 5, will, as long as it is inserted, offer support on each side of the urethra, just as the support was temporarily offered with the Bonney maneuver.

As can be seen from FIG. 2, the inflation tube 16 and valve 24 are stored between the top and bottom surfaces of the body 12. This will also occur in the design shown in FIG. 5. If necessary, the position of the diaphragm may be lowered somewhat if necessary in order to insure that this desired storage is accomplished.

As can be seen from FIG. 5, the elastic tube 16 is connected to the body 36 in the same manner as it is in the embodiment shown in FIGS. 1 and 2. Thus, the body 36 is provided with a stem 36.6, and the end 16.1 of the tube 16 is heat sealed within the stem 36.6.

While a preferred form of this invention has been described above and shown in the accompanying drawings, it should be understood that the applicant does not intend to be limited to the particular details described above and illustrated in the accompanying drawings, but intends to be limited only to the scope of the invention as defined by the following claims.

What is claimed is:

1. A vaginal pessary which is easier to insert and remove for cleaning, which has all parts in the vagina when inserted, and which does not give the wearer of the pessary significant discomfort during use, the volume of the pessary being reducible from its normal operational volume for relatively easy insertion and removal; said pessary comprising:

a hollow annular body for insertion into the vagina, the body having an exterior surface capable of contacting the walls of the vagina when having its normal operational volume so that relative movement of the hollow body with respect to the vagina is restricted;

elongated means for permitting inflation or deflation of the annular body, the elongated means including an elongated tube having first and second ends, the first end being connected to the hollow body in such a manner that a fluid can flow through the tube to or from the hollow body whereby the volume of the body may be changed, the tube being of such a length that, when fully extended, the second end of the tube will extend outwardly of the vagina when the annular body is properly inserted in the body; and means for maintaining the elongated means within the vagina when the pessary has been properly inserted into the vagina, the means for maintaining the elongated means within the vagina including coil means for imparting a coiled shape to the elongated tube when it is released to cause the tube to retract within the vagina.

2. The vaginal pessary as set forth in claim 1 wherein the coil means comprises tubing material having a coil memory.

3. The vaginal pessary as set forth in claim 1 wherein the coil means is a spring wire carried by the tube.

4. The vaginal pessary as set forth in claim 1 wherein the elongated means further includes a valve assembly located at the outer end of the elongated tube, the valve assembly normally being maintained in a closed position but being shifted into an open position when it is desired to either inflate or deflate the annular body, wherein the elongated tube is formed from an elastic material, the valve assembly including a rigid tube having an inner diameter greater than a portion of the inner diameter of the elastic tube, the rigid tube having a first flanged end and a second end, and the rigid tube being completely disposed within the free end of the elongated tube in such a manner that the elastic tube has first and second portions having conical inner surfaces disposed adjacent the first and second ends of the rigid tube, respectively, a spring having first and second ends, the first end of the spring bearing against the first flanged end of the rigid tube, a valve member slidable within the rigid tube, the valve member having first and second ends, the second end of the spring bearing against the first end of the valve member to normally force the second end of the valve member into contact with the conical inner surface of the second portion of the elastic tube to close said valve assembly.

5. A vaginal pessary which is easier to insert and remove for cleaning, which has all parts in the vagina when inserted, and which does not give the wearer of the pessary significant discomfort during use, the volume of the pessary being reducible from its normal operational volume for relatively easy insertion and removal; said pessary comprising:

a hollow annular body for insertion into the vagina, the body having an exterior surface capable of contacting the walls of the vagina when having its normal operational volume so that relative movement of the hollow body with respect to the vagina is restricted;

elongated means for permitting inflation or deflation of the annular body, the elongated means including an elongated inflation tube having first and second ends, the first end being connected to the hollow body in such a manner that a fluid can flow through the tube to or from the hollow body whereby the volume of the body may be changed, the tube being of such a length that, when fully extended, the second end of the tube will extend outwardly of the vagina when the annular body is properly inserted in the body; and means for maintaining the elongated means within the vagina when the pessary has been properly inserted into the vagina, the means for maintaining the elongated means within the vagina including support means carried by the annular body, said support means is a diaphragm extending between the inner surface of the annular body, said diaphragm being provided with an aperture.

6. The vaginal pessary as set forth in claim 5 wherein the elongated means being capable of being digitally manipulated so that it can be pushed through the aperture at the completion of the installation of the annular body and so that the elongated means may be also pulled out through the aperture when it is desired to reduce the volume of the annular body for removal.

7. A vaginal pessary which is easier to insert and remove for cleaning, which has all parts within the vagina when inserted, and which does not give the wearer of the pessary significant discomfort during use, the volume of the pessary being reducible from its normal operational volume for relatively easy insertion and removal; the pessary comprising:

a hollow annular body for insertion into vagina, the body having an exterior surface capable of contacting the walls of the vagina when having its normal operational volume so that relative movement of hollow body with respect to the vagina is restricted;

elongated means for permitting inflation or deflation of the annular body, the elongated means including an elongated tube having first and second ends, the first end being connected to the hollow body in such a manner that a fluid can flow through the tube to or from the hollow body whereby the volume of the body may be changed, the tube being of such a length that, when fully extended, the second end of the tube will extend outwardly of the vagina when the annular body is properly inserted within the vagina; and means for maintaining the elongated means within the vagina when the pessary has been properly inserted, the means for maintaining the elongated means within the vagina including coil means for imparting a coiled shape to the elongated tube when it is released to cause the tube to retract within the vagina, and support means carried by the annular body for supporting the elongated means within the vagina when the pessary has been properly inserted into the vagina, the support means being a diaphragm which extends between interior surfaces of the annular body, the diaphragm being provided with an aperture through which the elongated means can pass.

8. The vaginal pessary as set forth in claim 7 wherein the elongated tube is formed from an elastic polyurethane material having a coil memory, the tube being provided with a valve assembly, wherein the valve assembly includes a rigid stainless steel tube having an inner diameter greater than a portion of the inner diameter of the polyurethane tube, the rigid stainless steel tube having a first flanged end and a second end completely disposed within the free end of the elongated tube in such a manner that the elastic tube has first and second conical portions disposed adjacent the first and second ends of the tube, a spring having first and second ends, the first end of the spring bearing against the first end of the rigid tube, a valve member in form of a stainless steel rod slidable within the stainless steel tube, the valve member having first and second ends, the second end of the spring bearing against the first end of the stainless steel rod to normally force the second end of the stainless steel rod into contact with the inner surface of said second portion of the elastic tube to normally close the valve.

9. A stress incontinence pessary which is easier to insert and remove for cleaning, which has all parts maintained within the vagina when inserted, and which will not interfere with urination when inserted, and which does not give the wearer of the pessary significant discomfort, the volume of the pessary being reducible from its normal operational volume for relatively easy insertion and removal; said pessary including:

a hollow annular body for insertion into the vagina, the body having an exterior surface capable of contacting the walls of the vagina when having its normal operational volume so that relative movement of the hollow body with respect to the vagina is restricted, the body including two spaced apart projections, there being a U-shaped surface between the projections, the projection being capable of supporting the vaginal tissue on each side of the urethra when the annular body is inserted into the vagina in such a manner that the tissue between the projections is stretched and can offer counter pressure when intraabdominal pressure is suddenly raised as occurs during coughing, sneezing, laughing, and physical exercise such that the intra-abdominal pressure is transmitted to the upper urethra so that the greatest difference between the intra-urethral and simultaneous bladder pressure remains positive regardless of the changes in intraabdominal pressure so continence is preserved; and fluid passageway means for permitting inflation or deflation of the annular body, the fluid passageway means including a flexible elongated tube, the flexible tube having a first end connected to the annular body and a second free end, the flexible tube being of such a length that when fully extended it will extend outwardly of the vagina when the annular body is properly inserted within the vagina;

wherein the improvement comprises means for supporting the flexible tube within the vagina when the annular body is properly inserted within the vagina, the support means including coil means for imparting a coiled shape to the elongated tube when it is released to cause the tube to retract within the vagina, and a diaphragm which extends between interior surfaces of the annular body, the diaphragm being provided with an aperture through which the tube means may pass.

* * * * *

UNITED STATES PATENT AND TRADEMARK OFFICE
CERTIFICATE OF CORRECTION

PATENT NO. : 5,224,494
DATED : July 6, 1993
INVENTOR(S) : Goran L. Enhorning

It is certified that error appears in the above-identified patent and that said Letters Patent is hereby corrected as shown below:

Col. 2, lines 54 & 55, delete "to the coiled shape, as the tube is made from a material having a coiled";
Col. 2, lines 59 - 61, delete "memory, and the tube tends to retract into the vagina. Digital manipulation may encourage the coiled";
Col. 4, lines 2 - 5, delete "means within the vagina may include having the elongated tube 16 assume a coiled shaped when released, an apertured diaphragm";
Col. 4, line 6, after "and", insert ---an---;
Col. 4, line 9, delete ", or, preferably, both. The coiled shape of the".

Signed and Sealed this

Twenty-second Day of February, 1994

Attest:

BRUCE LEHMAN

Attesting Officer

Commissioner of Patents and Trademarks